United States Patent [19]
Payne et al.

[11] Patent Number: 5,253,312
[45] Date of Patent: Oct. 12, 1993

[54] OPTICAL FIBER TIP FOR USE IN A LASER DELIVERY SYSTEM AND A METHOD FOR FORMING SAME

[75] Inventors: Errol Payne, Newport Beach; Paul Mikus, Laguna Niguel, both of Calif.

[73] Assignee: Cytocare, Inc., Irvine, Calif.

[21] Appl. No.: 904,824

[22] Filed: Jun. 26, 1992

[51] Int. Cl.$^5$ .......................... G02B 6/02; B05D 5/06; B24B 1/00

[52] U.S. Cl. ......................................... 385/31; 385/38; 385/51; 385/85; 385/123; 385/147; 385/901; 427/163; 606/11; 606/15; 606/16; 606/18; 51/283 R

[58] Field of Search ........................ 385/31, 38, 51, 48, 385/85, 84, 115, 116, 117, 118, 119, 147, 901, 902; 427/163; 51/283 R, 284 E; 606/2, 10, 11, 15, 16, 17, 18

[56] References Cited

U.S. PATENT DOCUMENTS

| | | | |
|---|---|---|---|
| 4,740,047 | 4/1988 | Abe et al. | 385/31 X |
| 4,865,417 | 9/1989 | Naohiro et al. | 385/123 X |
| 5,164,945 | 11/1992 | Long et al. | 385/31 X |
| 5,179,610 | 1/1993 | Milburn et al. | 385/31 X |

FOREIGN PATENT DOCUMENTS 0163266 12/1985 European Pat. Off. .......... 385/31 X

*Primary Examiner*—Brian Healy
*Attorney, Agent, or Firm*—Lyon & Lyon

[57] ABSTRACT

An optical fiber tip for use in a laser delivery system comprising a distal end of an optical fiber having an exposed cylindrical core. A flat elliptical surface is formed across a distal end of said cylindrical core and intersects a center line of said cylindrical core at a predetermined angle. In one embodiment, a reflective coating is deposited on said flat elliptical surface such that a laser beam carried by said fiber will be reflected by said reflective coating. In another embodiment, said flat elliptical surface intersects said center line of said cylindrical core at an angle exceeding a critical angle necessary for said flat elliptical surface to totally reflect a laser beam carried by said optical fiber.

2 Claims, 9 Drawing Sheets

90° - A1

OPTICAL FIBER TIP FOR USE IN A LASER DELIVERY SYSTEM AND A METHOD FOR FORMING SAME

BACKGROUND OF THE INVENTION

The field of the present invention is laser energy delivery systems and, in particular, side firing fiber optic laser delivery systems.

Recent attention has been directed to the use of lasers in medical and dental applications. In particular, because the energy output of a laser may be precisely controlled and the thermal absorption of a given tissue area may be accurately predicted, it has been recognized by those skilled in the art that the laser provides an excellent means for causing a predictable amount of thermal damage to diseased or traumatized tissue.

It has also been recognized by those skilled in the art that optical fibers provide an excellent means for delivering laser radiation with minimal energy loss to remote tissue locations within a person's body. To this end, fiber optic laser delivery systems have been developed for use in numerous medical applications including the treatment of urological disorders, gastro-intestinal disorders, and vascular disorders. In fact, those in the medical community will recognize that fiber optic laser delivery systems may be used to deliver laser radiation to any tissue location which is accessible using a catheter, a scope, or a needle. The challenge, however, is to deliver the laser radiation to an identified tissue area in a useful and manageable form.

Conventional fiber optic laser delivery systems generally fall within one of two broad classes, contact systems and free beam systems. Contact systems, as the name suggests, utilize a contact element (i.e. an optical fiber tip or a lens element), which is placed in contact with a tissue area to be irradiated, and a beam carried by the fiber is delivered to the tissue at the point of contact. One exemplary type of contact system is the "ball tipped" system, which generally comprise an optical fiber tip having an exposed core region which is formed into the shape of a ball. In use, the ball of the fiber tip is placed in contact with the tissue to be irradiated, and substantially all of the energy delivered to the tip of the fiber is delivered to the tissue at the point of contact. It will be noted by those skilled in the art that, because the radiation passes directly from the laser fiber to the tissue to be treated, only a minimal amount of energy is lost at the tissue-fiber interface. However, because substantially all of the laser energy is delivered to the tissue at the point of contact (i.e. because substantially all of the laser energy is delivered to an extremely small tissue area), the use of contact delivery systems often results in excessive tissue vaporization and carbonization, thus making it quite difficult to treat large tissue areas in an even fashion.

Free beam laser delivery systems generally provide a means for directing a laser beam externally of a fiber toward a tissue area to be irradiated. In doing so, these systems provide a means for treating relatively large tissue areas (i.e. areas of 3-5 mm$^2$). If a free beam delivery system emits a beam to one side of a fiber or fiber tip assembly, the system will commonly be referred to as a "side-firing" laser delivery system. Side-firing systems laser delivery systems generally comprise an optical fiber having a reflector or prism assembly mounted at one end. The reflector or prism assembly is formed and positioned to deflect a laser beam carried by the fiber to one side of the fiber.

One example of such a side-firing system is the LATERALASE system manufactured by Trimedyne, Inc., of Tustin Calif. The LATERALASE system is designed for use in conjunction with a neodymium-YAG (Nd-YAG) laser and comprises an optical fiber having an aluminum reflector assembly mounted at one end. The reflector assembly includes a gold coated reflective surface which is positioned and shaped to cause a laser beam emitted by the tip of the fiber to diverge and to be deflected to one side of the fiber. Presently, the laser beam is deflected 90°, but the angle of deflection may vary. Because the position and orientation of the fiber and tip assembly may be precisely controlled, the LATERALASE system may be used to cause an even and predictable amount of thermal damage to a relatively large area of tissue.

Although the LATERALASE system has been well received by the medical community, those skilled in the art will recognize that the utility of the LATERALASE system is inherently limited in two respects. First, because the gold reflective surface is not capable of total reflection of the Nd-YAG beam (the surface is roughly 98.5% reflective at the 1.06 micron wavelength), the reflective surface tends to "heat up" during use. Accordingly, as the power output of the laser is increased, the likelihood of melting the reflective gold coating increases. Once the reflective gold coating melts, continued firing of the laser may cause the reflector assembly to melt.

Another example of a side-firing laser delivery system is the TULIP system, manufactured by Intrasonix, Inc., of Burlington, Mass. In contrast to the LATERALASE system, the TULIP device utilizes a prism assembly mounted to the tip of an optical fiber to deflect a beam to the side of the fiber. Those skilled in the art will note, however, that a prism capable of bending light at a 90° angle must be constructed from glass or another substance having a relatively high index of refraction, and that glasses having the required index of refraction tend to absorb energy at a wavelength of 1.06 microns (the Nd-YAG wavelength). Thus, because conventional prisms assemblies tend to absorb energy at the 1.06 micron wavelength, they too tend to retain heat during use and cannot be used to deliver a Nd-YAG laser beam at high power levels. For this reason, the TULIP system is recommended for use in the 20-40 watt power range, and has a maximum power rating of 60 watts.

It follows, based on the above discussion, that a need exists for a side-firing laser delivery system which minimizes media transition energy losses and, more importantly, a need exists for a side-firing laser delivery system which can operate efficiently at high power outputs.

SUMMARY OF THE INVENTION

The present invention is directed to an optical fiber tip for use in an improved "side-firing" fiber optic laser delivery system and to a method for constructing the same. To this end, an exemplary embodiment of the invention comprises an optical fiber tip which is modified to deflect a beam carried within the fiber at a prescribed angle to one side of the fiber, and which is shaped to cause the laser beam to diverge upon its exiting the fiber.

In one preferred embodiment, the optical fiber tip comprises a distal end of an optical fiber which has a partially exposed cylindrical core. The exposed core is cut at a prescribed angle yielding a flat elliptical surface which extends across the diameter of the core, and a reflective alloy is deposited over the flat elliptical surface, thus forming an elliptical reflector which is bonded directly to the core. It follows that a laser beam traveling within the optical fiber will be deflected by the elliptical reflector and will exit the core at a predetermined angle relative to the fiber. Because the beam is deflected by the reflective surface prior to its exiting the fiber, energy losses resulting from medium transitions are minimized.

In a second preferred embodiment, the optical fiber tip also comprises a distal end of an optical fiber having a partially exposed core, and again the core is cut at a prescribed angle yielding a flat elliptical surface which extends across the diameter of the core. In this instance, however, the flat elliptical surface is polished until it becomes optically reflective, and the prescribed angle at which the core is cut is determined based on Snell's Law (taking into account the index of refraction of the silica core and the index of refraction of the fiber operating environment) such that a laser beam traveling within the fiber will be totally reflected by the optically reflective surface. Because the laser beam is totally reflected by the optically reflective surface, the fiber tip absorbs essentially no energy and retains essentially no heat during use. Accordingly, side-firing laser delivery systems utilizing the second preferred form of the present invention may be used to deliver laser radiation at power levels greatly exceeding those attainable using prior art systems.

Accordingly, it is an object of the invention to provide an optical fiber tip for use in an improved "side-firing" fiber optic laser delivery system and to provide a method for making the same.

BRIEF DESCRIPTION OF THE DRAWINGS

FIG. 5(a) provides an illustration of an optical fiber mounted in a quartz holding tube prior to the tip grinding operation.

DESCRIPTION OF THE PREFERRED EMBODIMENTS

Figure 1A:
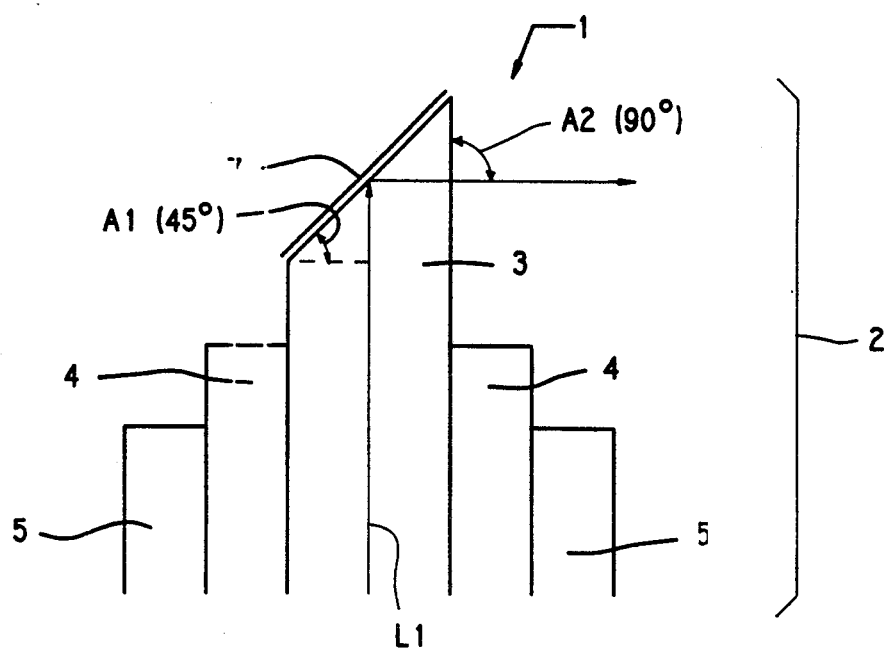
FIG. 1(a) is a cross-sectional view of a fiber optic tip in accordance with a first preferred embodiment of the invention.

Turning to the drawings, FIGS. 1(a) and (b) provide illustrations of an optical fiber tip 1 embodying a first preferred form of the invention. The optical fiber tip 1 comprises a distal end of a standard optical fiber 2 which may be purchased in a number of sizes (core diameters) from any one of a number of optical fiber suppliers, including 3M Medical Systems, Inc., of Westhaven, Conn. The optical fiber 2 comprises a cylindrical fused silica core 3, a silicone resin fiber cladding 4, and a plastic buffer coating 5. The fiber cladding 4 and the buffer coating 5 are removed from the distal tip of the optical fiber 2 to expose approximately a 1.5 mm length of the core 3. The core 3 is cut at a prescribed angle A1 (45° as illustrated in FIG. 1(a)) yielding a flat elliptical surface S1, and the flat elliptical surface S1 is polished and coated with a reflective alloy coating (not shown), thus forming an elliptical reflector 7 which is bonded to the core 3. In a preferred form, the flat elliptical surface S1 is polished until it becomes smooth to $10^{-4}$ inch. Further, the preferred reflective alloy coating comprises three layers, an aluminum oxide ($AlO_3$) base layer which acts as a binding agent, a silver (Ag) reflecting layer, and an aluminum oxide ($AlO_3$) protective coating layer. The aluminum oxide layers have a purity of 99.8% and are 850 angstroms thick. The silver layer is 98.9% reflective at the 1.06 micron wavelength, has a purity of 99.99%, and is 1800 angstroms thick. It will be noted by those skilled in the art that the reflective layer may be formed using any of a number of reflective substances including, for example, gold or copper.

In use, the elliptical reflector 7 deflects a laser beam L1 carried by the optical fiber 2 at a prescribed angle A2 (90° as illustrated) relative to the optical fiber 2. Further, as the laser beam L1 exits the side wall 9 of the cylindrical core 3, the side wall 9 acts as a conical lens and causes the laser beam L1 to diverge. Accordingly, by performing the functions of beam bending and beam divergence, the optical fiber tip 1 eliminates the need for independent reflector and prism assemblies in side-firing fiber optic laser delivery systems. Further, because the laser beam L1 is deflected prior to its exiting the core 3, energy losses resulting from medium transitions are minimized.

Those skilled in the art, however, will note that, because the silver reflecting layer of the reflective alloy coating is only 98.9% reflective at the 1.06 micron wavelength, the optical fiber tip 1 will absorb energy and retain heat when used in conjunction with a Nd-YAG laser. Thus, care must be taken to insure that the reflective alloy coating does not melt during use. To minimize the heating of the reflective alloy coating which occurs during use, it is suggested to position the tip 1 within the path of flow of an irrigating solution. In doing so, the basic principles of heat transfer are employed to dissipate any heat which may be imparted to the tip 1 by the laser beam L1. However, it should be understood that the use of an irrigating solution to cool the reflective alloy coating of the optical fiber tip 1 only minimizes the heating of the optical fiber tip 1. The tip heating problem is not solved entirely.

Figure 2A:
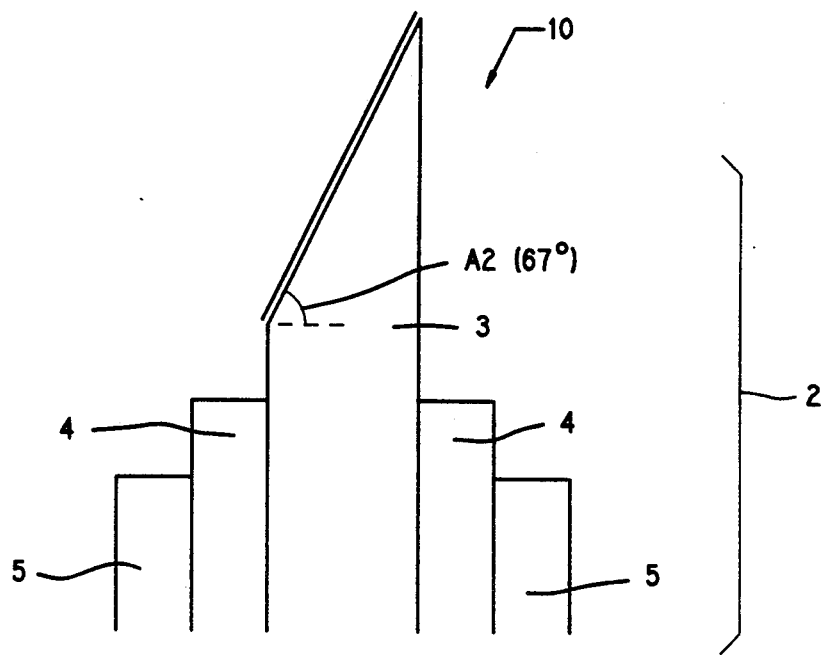
FIG. 2(a) is a cross-sectional view of a fiber optic tip in accordance with a second preferred embodiment of the invention.

Turning now to FIGS. 2(a) and (b), a second preferred embodiment of the invention is disclosed which solves the tip heating problem by eliminating the reflective alloy coating and increasing the angle A1 at which the core 3 is cut to take advantage of the phenomenon commonly referred to as total internal reflection.

Figure 3A:
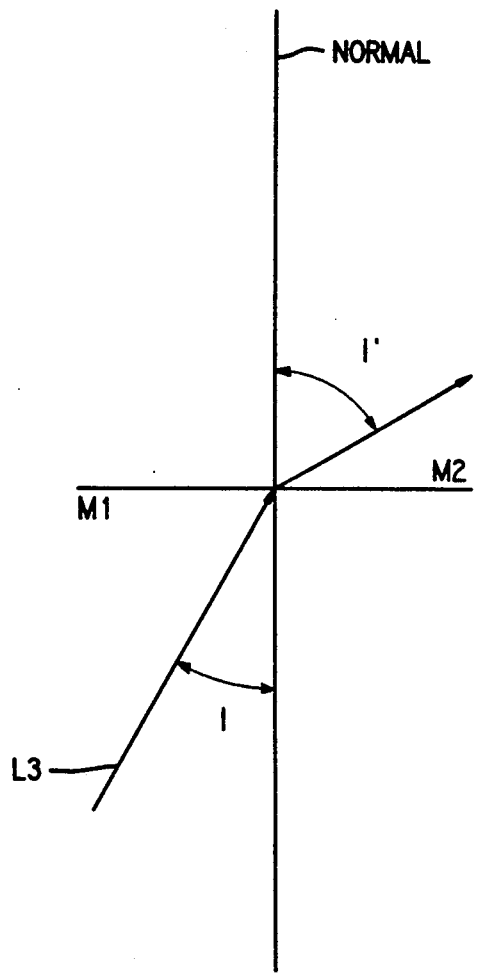
FIG. 3(a) provides an illustration of a light wave intersecting an interface between a medium having a higher index of refraction and a medium having a lower index of refraction.
Figure 3B:
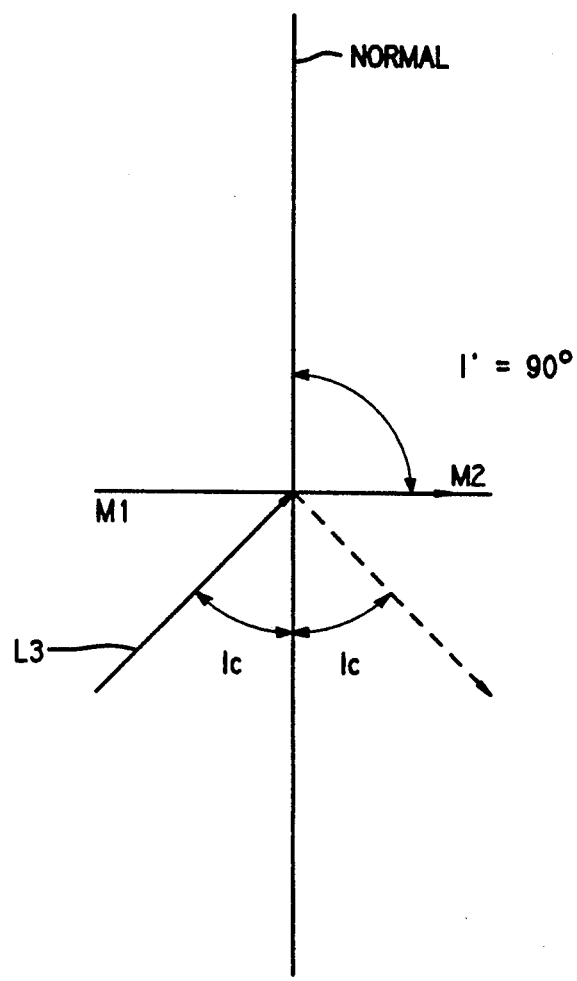
FIG. 3(b) provides an illustration of a light wave which intersects an interface between a medium having a higher index of refraction and a medium having a lower index of refraction at the critical angle.

As illustrated in FIGS. 3(a) and (b), when a light ray L3 (in this case a laser beam) passes from one medium M1 having a higher index of refraction (N) to another medium M2 having a lower index of refraction (N'), the light ray L3 is refracted away from a normal to the interface between the media M1 and M2. The relationship between the angle of incidence I and the angle of refraction I' is governed by Snell's Law, which is set forth in equation (1).

$$\sin I' = N/N'(\sin I) \tag{1}$$

Accordingly, as the angle of incidence I is increased, the angle of refraction I' increases at a greater rate. However, once the angle of incidence I reaches a value such that (sin I)=N'/N, the angle of refraction I' will become 90°. At this point, none of the light ray L3 is transmitted through the interface between the two media M1 and M2. Instead, the light ray L3 is totally reflected back into the medium M1 having the higher index of refraction N. The angle of incidence I at which (sin I)=N'/N is referred to as the critical angle $I_c$, because any light ray L3 travelling within the medium M1 which intersects the interface between the two media M1 and M2 at an angle equal to or greater than the critical angle $I_c$, will be totally reflected back into the medium M1.

Figure 4:
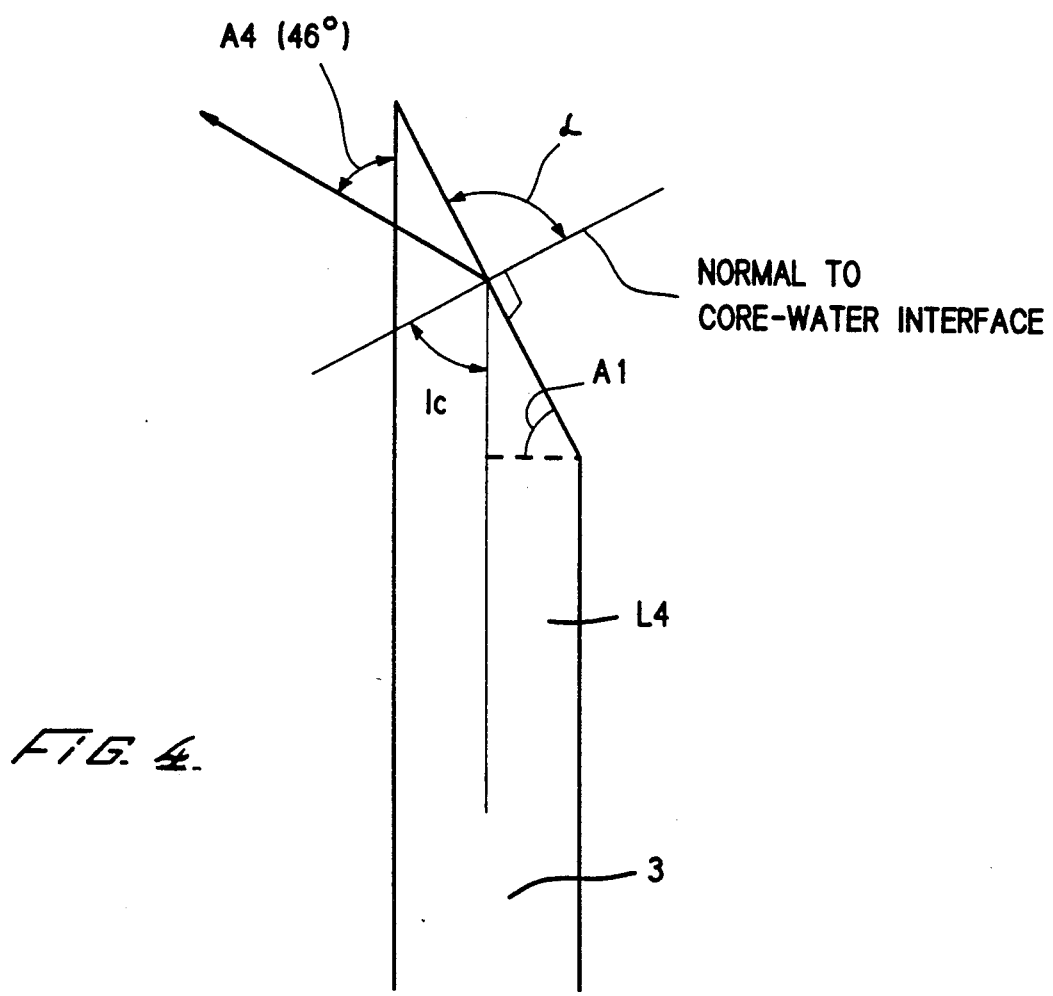
FIG. 4 provides an illustration of an optical fiber core in accordance with a second preferred embodiment of the invention.
Figure 5B:
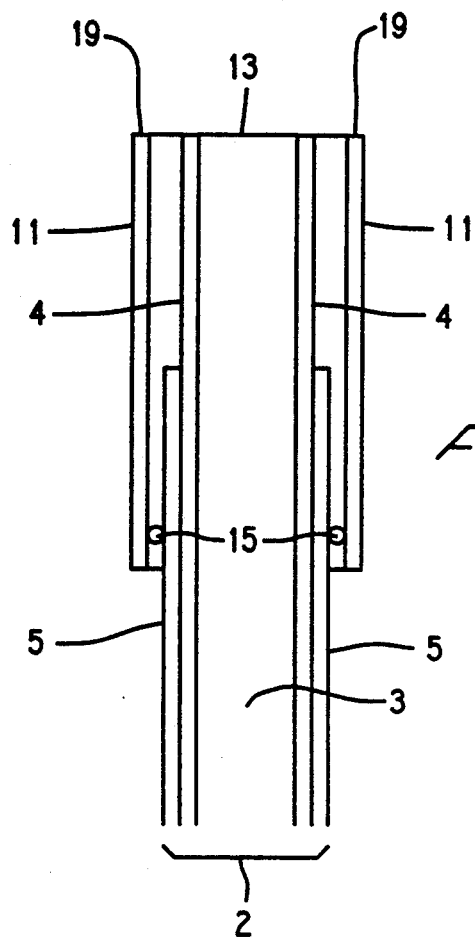
FIG. 5(b) provides an illustration of a staging fixture for use in grinding the tip of an optical fiber.
Figure 5C:
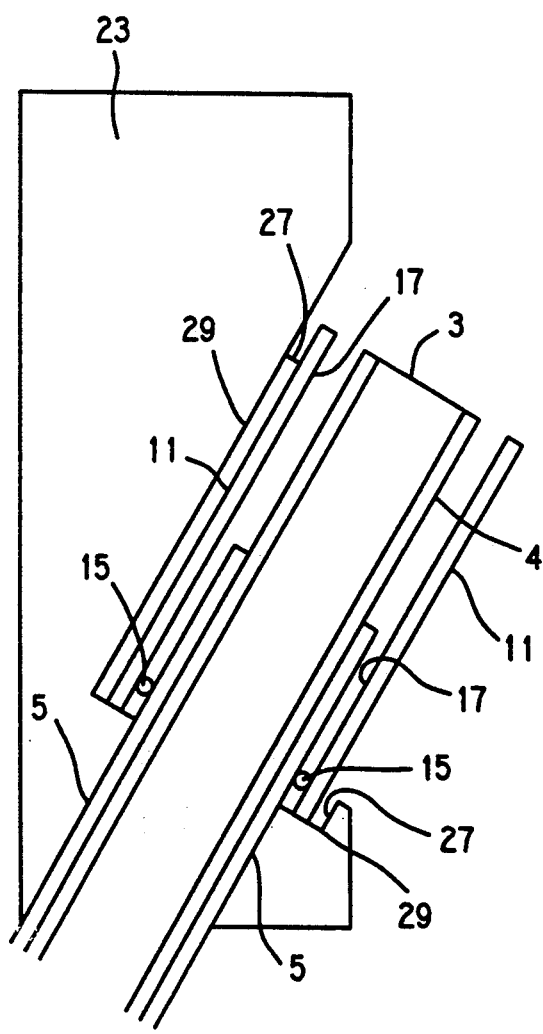
FIG. 5(c) provides an illustration of the mounting of an optical fiber and a quartz holding tube in a staging fixture prior to the tip grinding operation.
Figure 5B:
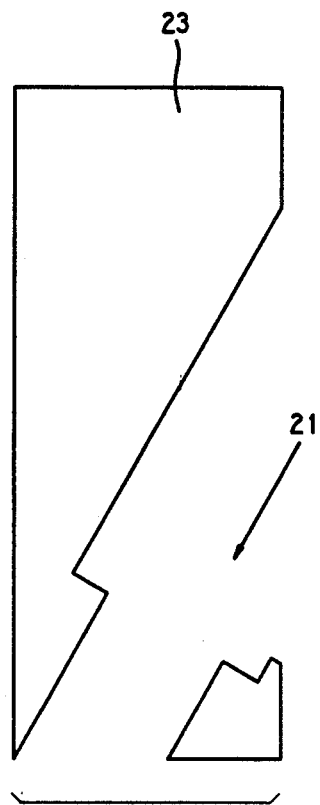
Figure 5D:
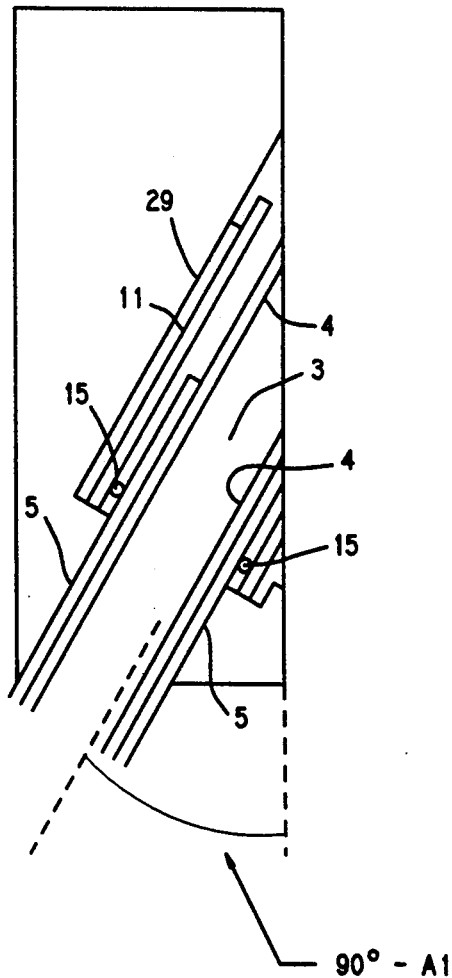
FIG. 5(d) provides an illustration of the mounting of an optical fiber and a quartz holding tube in a staging fixture after the tip grinding operation.

Turning again to FIGS. 2(a) and (b), the optical fiber tip 10 of the second embodiment comprises a distal end of a standard optical fiber 2 which, as set forth above, may be purchased in a number of sizes (core diameters) from any of a number of optical fiber suppliers including 3M Medical Systems, Inc., of Westhaven, Conn. The optical fiber 2 comprises a cylindrical fused silica core 3, a silicone resin fiber cladding 4, and a plastic buffer coating 5. In a preferred form, the core 3 of the optical fiber 2 has an index of refraction of at least 1.456, and the cladding 4 has an index of refraction of approximately 1.40. The fiber cladding 4 and the buffer coating 5 are removed from the distal tip of the optical fiber 2 to expose approximately a 2.5 mm length of the core 3. The angle A1 at which the core 3 must be cut to achieve total internal reflection is determined in accordance with Snell's Law (i.e. by determining the critical angle $I_c$ at the interface between the core 3 and the anticipated operating environment), and that calculation is set forth below with reference to FIG. 4. The index of refraction $N_g$ of the core 3 of a standard optical fiber 2 is substantially 1.456, and the index of refraction $N_w$ of water (an exemplary operating environment) is substantially 1.33.

Snell's Law:

$$\sin I_c = N_g/N_w(\sin \alpha)$$

$$I_c = \arcsin N_g/N_w(1), \text{ where } \alpha = 90°$$

$$I_c = \arcsin 1.456/1.33$$

$$I_c = 65.98°$$

$$I_c \angle A1; A1 = 65.98°$$

To compensate for surface variations at the water-core interface, the angle A1 at which the core is cut is increased to 67°. Thus, all parallel rays L4 traveling within the optical fiber 2 will be totally reflected by the interface between the core 3 and the water operating environment. The angle A4 at which the rays L4 are deflected relative to the fiber is substantially 46°. To further insure that substantially all of the rays L4 are deflected by the interface between the core 3 and the water operating environment, the elliptical surface S2, which is produced upon cutting the core 3, is polished until it is smooth to $10^{-4}$ inch. Divergence of the laser beam (parallel rays L4) is accomplished as set forth above. The side wall 9 of the cylindrical core 3 acts as a conical lens and causes the deflected rays L4 to diverge. It should now be appreciated that the fiber optic tip 10 of the second embodiment provides a highly useful and efficient means for deflecting and diverging high energy laser beams, as the interface between the core 3 and the water operating environment will reflect substantially 100% of a laser beam back into the core 3 and, more importantly, the interface will therefore absorb no heat during use.

Turning now to FIGS. 5(a)-(d), the method of constructing the optical fiber tips 1 and 10 of the preferred embodiments will be described in detail. As stated above, the optical fiber tips 1 and 10 are constructed at the distal end of a standard optical fiber 2. The size (core diameter) of the optical fiber 2 may vary, however, fibers 2 having a 600, 800, or 1000 micron core diameter are presently preferred. After an optical fiber 2 is selected, the fiber 2 is inserted into a quartz holding tube 11 having an inside diameter of substantially 2 mm, and a length of substantially 0.5 cm of the buffer coating 5 is stripped away from the distal end 13 of the fiber 2 using conventional means. Next, an O-ring 15 is placed around the fiber 2 to form a seal between the buffer coating 5 of the fiber 2 and the inner wall 17 of the quartz holding tube 11, and the position of the fiber 2 within the holding tube 11 is adjusted such that the distal end 13 of the core 3 is substantially adjacent the distal end 19 of the holding tube 11. Next, the fiber holding tube 11 is inserted into an aperture 21 located in a staging fixture 23. The aperture 21 is shaped such that a proximal region of the holding tube 11 may be fitted securely in the aperture 21, and such that a small gap 27 is formed between the holding tube 11 and the inner wall 29 of the aperture 21. A liquid metal alloy is then injected into the gap 27 and the distal end 19 of the holding tube 11 to secure the optical fiber 2 in the holding tube 11 and the holding tube 11 in the staging fixture 23. It is preferable to use a metal alloy having a melting point of substantially 150° F. for securing the optical fiber 2 in the staging fixture 23. The presently preferred alloy for securing the optical fiber 2 and the holding tube 11 in the staging fixture 23 is CERRO-BEND METAL, which is manufactured by Cerro Metal Products, Inc., of Bellefonte, Pa. However, those skilled in the art will recognize that CERRO-BEND METAL is only one of a number of metals and alloys which may be used to secure the optical fiber 2 in the staging fixture 23.

Figure 1B:
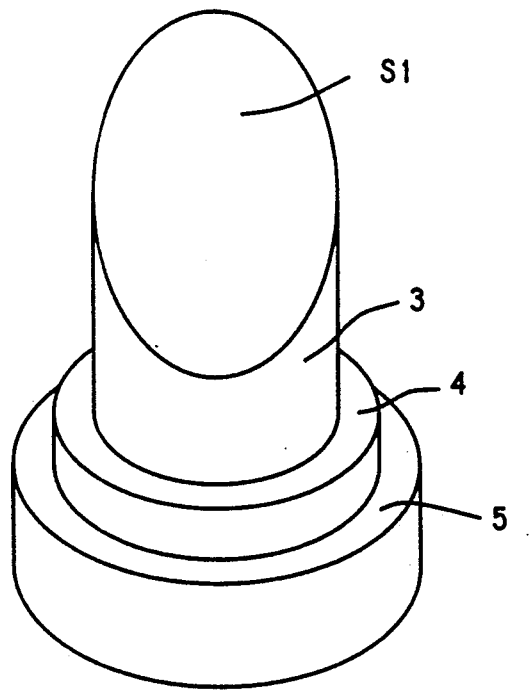
FIG. 1(b) is a side view of a fiber optic tip in accordance with a first preferred embodiment of the invention.
Figure 2B:
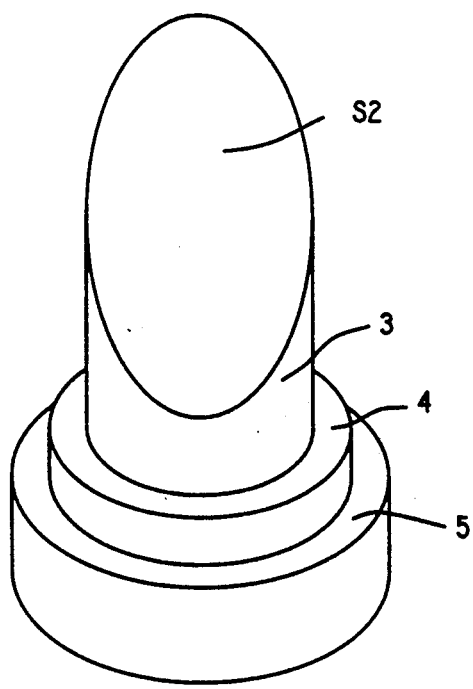
FIG. 2(b) is a side view of a fiber optic tip in accordance with a second preferred embodiment of the invention.

Once the optical fiber 2 is secured in the staging fixture 23, e.g. once the metal alloy cools and solidifies, the staging fixture 23 is placed on a standard Blanchard grinder (not shown), and a gross grinding is performed to cut the optical fibers at the prescribed angle A1 (shown in FIGS. (a) and (b), 2(a) and (b), and 4). After the initial grinding is performed, the staging fixture 23 is removed from the grinder and placed in a lap or polisher (not shown), and the flat elliptical surface S or S2 (shown in FIGS. 1(b) and 2(b)), which was formed at the distal end of the core 3 during the grinding operation, is polished using conventional means until it is smooth to $10^{-4}$ inch. Those skilled in the art will note, however, that if a reflective coating is to be used to deflect the laser beam L1 (as illustrated in FIG. 1) it is not necessary to polish the flat elliptical surface S1 to this extent. After the polishing process is complete, the staging fixture 23 is removed from the lap and placed in a hot water bath (not shown). The heat from the water causes the metal alloy to melt, and the optical fiber 2 is then removed from both the holding tube 11 and the staging fixture 23.

Figure 6:
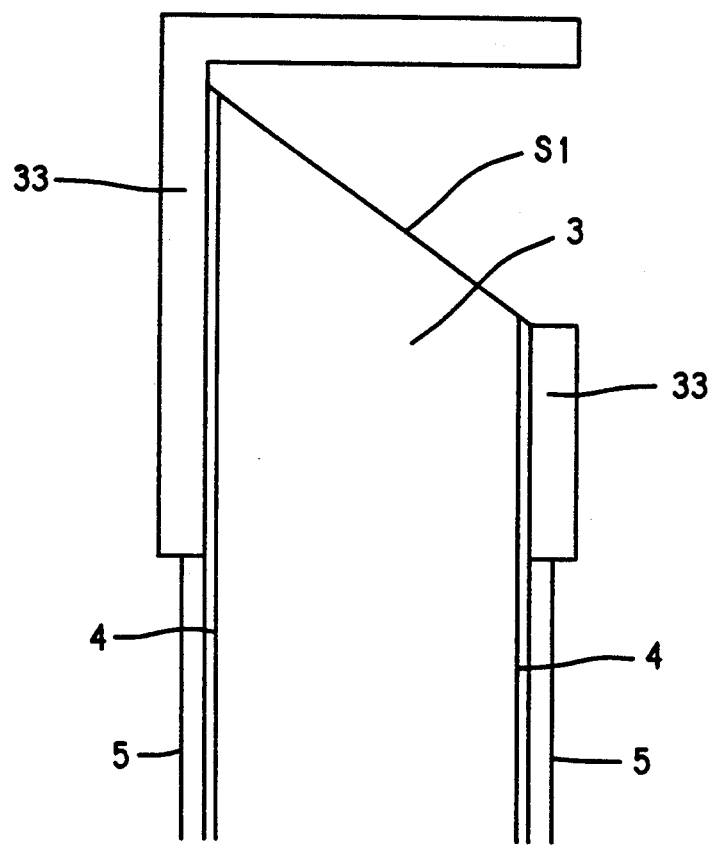
FIG. 6 provides an illustration of a tooling fixture used in depositing a reflective coating onto an optical fiber tip.

If it is desired to apply a reflective coating to the flat elliptical surface S1, the optical fiber 2 is then placed in a second tooling fixture 33 (illustrated in FIG. 6), and the tooling fixture 33 and the fiber 2 are placed in a standard ambient temperature coating chamber (not shown), wherein each layer of the reflective coating is deposited on the flat elliptical surface S1. As set forth above, in the preferred embodiment a first aluminum oxide ($AlO_3$) layer having a purity of 99.8% and a thickness of substantially 850 angstroms is deposited on the flat elliptical surface S1. The first aluminum oxide ($AlO_3$) layer acts as a binding agent for the silver (Ag) reflective layer which is deposited next. The silver reflective layer has a purity of 99.99% and is substantially 1800 angstroms thick. Last, a second aluminum oxide ($AlO_3$) layer is deposited over the silver layer to form a protective coating.

Figure 7A:
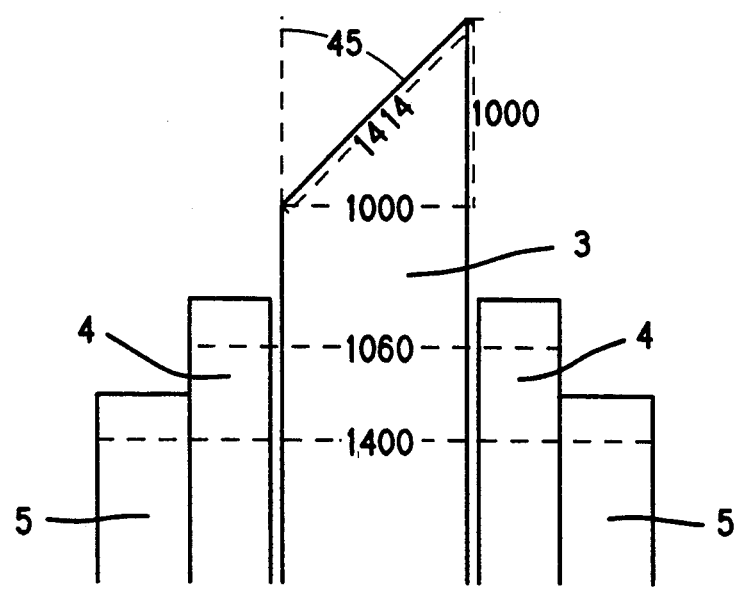
FIG. 7(a) illustrates the dimensions of an exemplary 1000 micron optical fiber modified in accordance with a first preferred form of the invention.
Figure 7B:
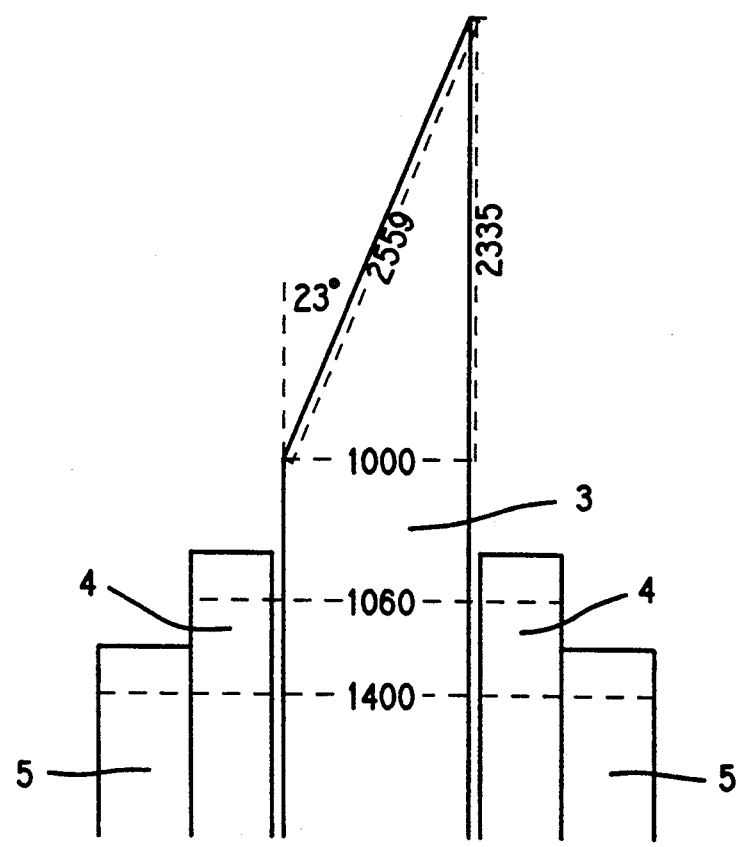
FIG. 7(b) illustrates the dimensions of an exemplary 1000 micron optical fiber modified in accordance with a second preferred form of the invention.

After the flat elliptical surface S1 or S2 is polished (and coated, if desired), the previously exposed cladding 4 is wiped away using acetone to expose a desired length of the wall 9 of the core 3. In the preferred embodiment, only that portion of the wall 9 which is opposite the flat elliptical surface S1 or S2 is exposed. This minimizes the potential for a laser beam to escape the core 3 prior to being reflected. The dimensions of an exemplary 1000 micron fiber, which has been modified in accordance with the preferred embodiments of the present invention, are illustrated in FIGS. 7(a) and (b).

While the invention is susceptible to various modifications and alternative forms, specific examples thereof have been shown by way of example in the drawings and are herein described in detail. It should be understood, however, that it is not intended to limit the invention to the particular forms disclosed, but to the contrary, the invention is to cover all modifications, equivalents, and alternatives falling within the scope of the appended claims.

What is claimed is:

1. A method of modifying an optical fiber for use in laser delivery systems, said optical fiber comprising a cylindrical core, a cladding layer surrounding said cylindrical core, and a buffer coating surrounding said cladding layer, said method comprising the steps of:

removing a first length of said buffer coating from a distal end of said optical fiber to expose a distal end of said cylindrical core and said cladding layer, positioning said optical fiber in a holding tube, positioning said holding tube in a staging fixture, said holding tube and said optical fiber forming a predetermined angle with a surface of said staging fixture, and a distal portion of said holding tube, said cladding layer, and said cylindrical core extending past said surface of said staging fixture, securing said optical fiber in said holding tube and securing said holding tube in said staging fixture by injecting a liquid metal alloy into said staging fixture and said holding tube, and allowing said metal alloy to solidify, mounting said staging fixture in a grinder, grinding said holding tube, said cladding layer, said cylindrical core, and said metal alloy until said distal portion of said holding tube, said cladding layer, and said cylindrical core is flush with said surface of said staging fixture, said grinding forming a flat elliptical surface across a distal end of said core, removing said staging fixture from said grinder, removing said holding tube from said staging fixture and removing said optical fiber from said tube, depositing a reflective coating on said flat elliptical surface, and removing a portion of said cladding layer opposite to said flat elliptical surface.

2. A method of modifying an optical fiber for use in laser delivery systems, said optical fiber comprising a cylindrical core, a cladding layer surrounding said cylindrical core, and a buffer coating surrounding said cladding layer, said method comprising the steps of:

removing a first length of said buffer coating from a distal end of said optical fiber to expose a distal end of said cylindrical core and said cladding layer, positioning said optical fiber in a holding tube, positioning said holding tube in a staging fixture, said holding tube and said optical fiber forming a predetermined angle with a surface of said staging fixture, and a distal portion of said holding tube, said cladding layer, and said cylindrical core extending past said surface of said staging fixture, securing said optical fiber in said holding tube and securing said holding tube in said staging fixture by injecting a liquid metal alloy into said staging fixture and said holding tube and allowing said metal alloy to solidify, mounting said staging fixture in a grinder, grinding said holding tube, said cladding layer, said cylindrical core, and said metal alloy until said distal portion of said holding tube, said cladding layer, and said cylindrical core is flush with said surface of said staging fixture, said grinding forming a flat elliptical surface across a distal end of said core, said flat elliptical surface intersecting a center line of said core at a first predetermined angle, said first predetermined angle being equal to or greater than a critical angle such that said flat elliptical surface is capable of totally reflecting a laser beam carried by said optical fiber, and such that said laser beam will be deflected at a second predetermined angle relative to said center line of said core, removing said staging fixture from said grinder, removing said holding tube from said staging fixture and removing said optical fiber from said tube, and removing a portion of said cladding layer opposite to said flat elliptical surface.

* * * * *